United States Patent [19]

Ozerov et al.

[11] Patent Number: 4,911,820

[45] Date of Patent: Mar. 27, 1990

[54] APPARATUS FOR MEASURING HYDROGEN CYANIDE VAPOR CONTENT IN THE AIR

[76] Inventors: Anatoly I. Ozerov, ultisa Dzhandosova, 69a, kv. 18; Vasily V. Gaditsky, ulitsa Internatsionalynaya, 133, kv. 38; Evgeny P. Kratsberg, ulitsa Auezova, 104a, kv. 4; Vladimir A. Slabinsky, ulitsa Baumana, 82, kv. 37; Irina P. Malakhova, ulitsa Dekarta, 34, kv. 2, all of Alma-Ata, U.S.S.R.

[21] Appl. No.: 231,703

[22] Filed: Aug. 12, 1988

[51] Int. Cl.⁴ .............................................. G01N 27/54
[52] U.S. Cl. ..................................... 204/431; 204/1 T
[58] Field of Search ................. 204/402, 431, 432, 1 N

[56] References Cited

U.S. PATENT DOCUMENTS 2,864,747 12/1958 Roth ...................................... 204/1 T

FOREIGN PATENT DOCUMENTS 976368 11/1982 U.S.S.R. .
2074323 10/1981 United Kingdom .

Primary Examiner—G. L. Kaplan
Attorney, Agent, or Firm—Ladas & Parry

[57] ABSTRACT

An apparatus for measuring hydrogen cyanide vapor content in the air having an electrode cell with an electrolyte which accommodates an indicator electrode with a sensor member, which is connected by means of a salt bridge with a comparison electrode immersed in the electrolyte, an amplifier, and a recorder, the electrode cell being divided by means of an ion exchange membrane into two compartments, the first compartment containing an electrolyte which is free from cyanide ions and accommodating the comparison electrode, the indicator electrode being positioned above the electrolyte level in the second compartment which also accommodates a means for supplying the electrolyte from the second compartment to the sensor member of the indicator electrode, said means ensuring supply of the electrolyte at regular intervals and being coupled to a compressor.

4 Claims, 1 Drawing Sheet

U.S. Patent    Mar. 27, 1990    4,911,820
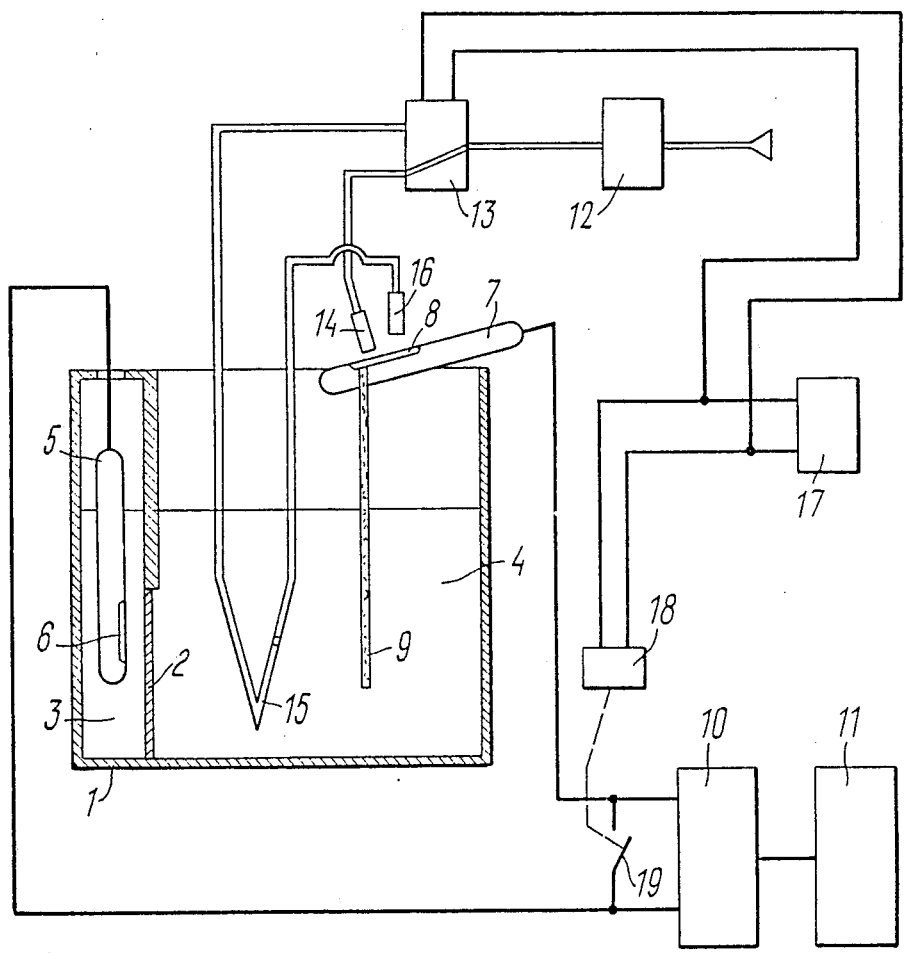

APPARATUS FOR MEASURING HYDROGEN CYANIDE VAPOR CONTENT IN THE AIR

FIELD OF THE INVENTION

The invention relates to electrochemical equipment for measuring chemical properties of the environment, and more specifically, it deals with apparatuses for measuring hydrogen cyanide vapour content in the air.

The invention may be used at any plants in the electrical and radio engineering and in chemical industries where installations containing cyanide solutions are used and where releases of toxic hydrogen cyanide vapour in the air of production premises cannot be completely avoided.

BACKGROUND OF THE INVENTION

Known in the art is a method of potentiometric measurement of microconcentrations of gases in the air and an apparatus for carrying out the method (SU, A, 976368). The apparatus comprises an electrode cell containing an electrolyte, an indicator electrode and a comparison electrode, an amplifier for determining a signal corresponding to hydrogen cyanide vapour content, and a recorder.

This apparatus cannot ensure the desired accuracy of measurement of hydrogen cyanide vapour content because of a gradual accumulation of cyanides in the electrolyte and a drift of the electrode function. It is also necessary to keep an eye on the electrolyte level in the electrolyte cell since a deviation of this level even by 1-2 mm from the pre-set value causes a disruption in operation of the apparatus.

Also known in the art is an apparatus for measuring hydrogen cyanide vapour content (GB, A 2074323), comprising an indicator electrode in the form of an ionselective electrode sensitive to cyanide ions, and a comparison electrode, each electrode having a sensor member, a salt bridge through which the indicator electrode is connected to the comparison electrode, a sealed electrode cell accommodating the indicator electrode having ports for admission and discharge of the air to be tested, and a means for supplying the electrolyte to the indicator electrode. The apparatus also has an amplifier for determining a signal corresponding to hydrogen cyanide vapour content, a compressor for supplying a continuous flow of the air to be tested to the electrode cell, and the means for supplying the electrolyte to the indicator electrode comprising a small-diameter tube open at one end, having its open end directed at the sensor member of the indicator electrode.

This apparatus has a number of disadvantages:

low speed because it takes much time to achieve a full change of an air batch in the electrode cell and because of adsorption of hydrogen cyanide vapour by the walls of the electrode cell, and a long time is needed for cyanide diffusion through a relatively thick electrolyte film (which is determined by surface tension of electrolyte) on the surface of the sensor member of the indicator electrode;

low accuracy of the analysis which is caused by instability of the electrolyte film under washing with electrolyte and by a drift of the electrode function of the indicator electrode;

low sensitivity which is caused by a relatively low partial pressure of hydrogen cyanide vapour over the electrolyte film on the surface of the sensor member of the indicator electrode and a certain loss of sensitivity because of chloride ions penetration from the salt bridge (when a single salt bridge is used); and difficulties in operation since frequent calibrations (once every 24 hours) are necessary, the electrolyte should be frequently prepared and poured (10 l in 2 to 15 days), and the salt bridges should also be maintained.

SUMMARY OF THE INVENTION

It is an object of the invention to increase speed of tests of the air to be tested.

It is also an object of the invention to improve accuracy of measurements.

Further object of the invention is to improve sensitivity of the apparatus.

Finally, it is an object of the invention to improve operation and maintenance.

These objects are accomplished by that in an apparatus for measuring hydrogen cyanide vapour content in the air, comprising an electrode cell containing an electrolyte and having an indicator electrode with a sensor member connected to a salt bridge containing an electrolyte, the indicator electrode being connected through the electrolyte to a comparison electrode immersed in the electrolyte, an amplifier having an input to which is connected the comparison electrode for determining a signal corresponding to hydrogen cyanide vapour content, a recorder having an input connected to an output of the amplifier, a means for supplying the electrolyte to the indicator electrode, a compressor, and a nozzle for supplying the air to be tested to the sensor member of the indicator electrode, according to the invention, the electrode cell is divided into two compartments by means of an ion exchange membrane, the first compartment containing an electrolyte which is free from cyanide ions, and the comparison electrode being located in this compartment, the indicator electrode being positioned above the level of the electrolyte in the second compartment which accommodate a means for supplying the electrolyte from the second compartment to the sensor member of the indicator electrode, said means ensuring the electrolyte supply at regular intervals and being coupled to the compressor.

It is preferred that in an apparatus for measuring hydrogen cyanide vapour content in the air, the means for the electrolyte supply comprise an air lift immersed in the electrolyte in the second compartment, and that the compressor be connected, via a switch, to an inlet of the air lift and to the nozzle for supplying the air to be tested to the sensor member of the indicator electrode, the switch connecting the compressor to the air lift in one position and to the nozzle in the other position.

It is also preferred that in an apparatus having a control unit, the switch be made in the form of an electromagnetic valve connected to a first output of the control unit, a second output of the control unit being connected to the winding of a relay having its normally open contacts connected to the indicator electrode and to the comparison electrode.

It is also preferred that in an apparatus, the sensor members of the indicator electrode and comparison electrode be made of gold.

The invention as described above features novel elements which ensure a high speed, simplicity of structure and operation and maintenance. The air to be tested is admitted to the inlet of the apparatus without prefiltering, and the electrolyte is repeatedly used and changed once-twice in a month only.

The complete measurement cycle takes 5 to 15 seconds only. The apparatus has an output to an external alarm system for giving an alarm if the permissable hydrogen cyanide vapour content in the air is overpassed, and it allows efficiency of ventilation of production premises to be monitored and makes it possible to control electric energy consumption for ventilation.

BRIEF DESCRIPTION OF THE DRAWING

The invention will now be described with reference to a specific embodiment illustrated in the accompanying drawing, which shows a general view of an apparatus for measuring hydrogen cyanide vapour content in the air, according to the invention.

DETAILED DESCRIPTION OF THE INVENTION

An apparatus for measuring hydrogen cyanide vapour content in the air comprises an electrode cell 1 filled with an electrolyte and divided by means of an ion exchange membrane 2 into two compartments 3 and 4. The first compartment 3, which is filled with an electrolyte free of cyanide ions, accommodates a comparison electrode 5 having a sensor member 6, and the second compartment 4 accommodates an indicator electrode 7 positioned above the electrolyte level and having a sensor member 8 which is connected, through a salt bridge 9, to the electrolyte, the indicator electrode 7 being electrically connected through the electrolyte to the comparison electrode 5. The comparison electrode 5 and the indicator electrode 7 are each connected to a respective input of an amplifier 10 for determining a signal corresponding to hydrogen cyanide vapour contect in the air, an output of the amplifier 10 being connected to a recorder 11. A compressor 12 is connected, via a switch 13, to a nozzle 14 by means of a flexible tube, the nozzle being designed for supplying the air to be tested to the sensor member 8 of the indicator electrode 7. In addition, the apparatus also has a means for the electrolyte supply comprising an air lift 15 immersed in the electrolyte in the second compartment 4, an inlet of the air lift being connected to the compressor 12 through the switch 13 which is made in the form of an electromagnetic valve, an outlet of the air lift being connected to a pipe 16 for supplying the electrolyte to the sensor member 8 of the indicator electrode 7, the switch 13 connecting the compressor 12 to the air lift 15 in one position and to the nozzle 14 in the other position. The apparatus for measuring hydrogen cyanide vapour content in the air also comprises an electronic control unit 17 having a first output connected to the switch 13 and a second output connected to the winding of a relay 18 having its normally open contacts 19 connected to the indicator electrode 7 and to the comparison electrode 5. The sensor members 6, 8 of the indicator electrode 7 and comparison electrode 5 are made of gold or silver sulfide.

The amplifier 10, recorder 11, compressor 12, switch 13 (electromagnetic valve), control unit 17, and relay 18 are widely known devices.

The apparatus for measuring hydrogen cyanide vapour content in the air functions in the following manner.

The apparatus has two modes of operation: measurement cycle and preparation cycle.

During the measurement cycle, the gas to be tested is supplied by the compressor 12, via the switch 13 (electromagnetic valve) and nozzle 14 to the sensor member 8 of the indicator electrode 7 having on the surface thereof a thin electrolyte film, no cyanides being available in the diffusion area of the film before the measurement cycle begins. Hydrogen cyanide vapour present in the air to be tested is trapped in the electrolyte film which a concentration of cyanide ions obtains which is proportional to their content in the air.

The difference of potentials between the indicator electrode 7 and the comparison electrode 5 is amplified in the amplifier 10 and recorded at the end of the measurement cycle, the duration of which is determined by the control unit 17 by the recorder 11 which causes actuation of an alarm system (light or audio alarm) if an ultimate permissable value is overpassed.

When the measurement cycle is over, the cycle of preparation of the apparatus for the next measurement cycle begins. The control unit 17 feeds a command for switching over the electromagnetic valve 13. The air supplied by the compressor 12 through the electromagnetic valve 13 actuates the air lift 15, and the sensor member 8 of the indicator electrode 7 is washed with the electrolyte supplied from the compartment 4 of the electrode cells 1. The electrolyte that flows down from the sensor member 8 of the indicator electrode 7 washes a cotton wick which forms the salt bridge 9 so as to form a galvanic circuit between the indicator electrode 7 and the electrolyte. Simultaneously with washing of the sensor member 8 of the indicator electrode 7 with the electrolyte and formation of a fresh thin layer of the electrolyte on the surface of the sensor member 8, the normally open contacts 19 of the relay 18 are closed. This results in cyanides supplied with the electrolyte being oxidized in the diffusion area of the indicator electrode 7. The oxidation occurs owing to a concentration difference of potentials between the indicator electrode 7 and comparison electrode 5 having their sensor members 6, 8 made of one and the same material. The cycle of preparation for measurement is thus over, and a new measurement cycle begins at the moment when there are no cyanides available in the diffusion area of the indicator electrode 7.

Therefore, the apparatus for measuring hydrogen cyanide content in the air allows thickness of the electrolyte film on the sensor member 8 of the indicator electrode 7 to be first reduced and then stabilized, and speed and accuracy of test to be improved. An increase in the partial pressure of hydrogen cyanide vapour over the surface of the indicator electrode 7 improves sensitivity of the apparatus as a whole. The use of the air lift 15 makes it possible to use the electrolyte repeatedly and ensures a comparatively accurate batching of electrolyte for each measurement cycle. Connecting together the indicator electrode 7 and the comparison electrode 5 at regular intervals allows cyanides available on the surface of the sensor member 8 of the indicator electrode 7 to be oxidized so as to begin the measurement cycle at the moment when there are no cyanides available in the diffusion area of the indicator electrode 7 thereby improving accuracy of the test and dispensing with the need to calibrate zero readings of the apparatus during the entire service life period.

The apparatus for measuring hydrogen cyanide vapour content in the air is capable of reacting simultaneously to several toxic gases (hydrogen cyanide vapour, hydrogen sulfide and carbon disulfide). In such applications, monitoring of the environment can be carried out using one and-the same apparatus. The speed of the apparatus according to the invention is higher than that of the state of the art apparatuses, whereby intoxication of personnel operating with plants for handling cyanide solutions is ruled out.

We claim:

1. An apparatus for measuring hydrogen cyanide vapor content in the air, said apparatus comprising:
   an electrode cell; an ion exchange membrane dividing said electrode cell into a first compartment and a second compartment;
   an electrolyte free of cyanide ions filling said first compartment;
   an electrolyte filling said second compartment;
   a comparison electrode having a sensor member immersed in said electrolyte free of cyanide ions in said first compartment;
   an indicator electrode having a sensor member and a salt bridge positioned above the level of said electrolyte in said second compartment, said electrode being electrically connected, via said salt bridge and said electrolyte of said second compartment free of cyanide ions in said first compartment, to said comparison electrode;
   a means for supplying said electrolyte from said second compartment, and means supplying said electrolyte to said sensor member of said indicator electrode at regular intervals;
   an amplifier for determining a signal corresponding to hydrogen cyanide vapor content, said amplifier having a first input connected to said comparison electrode, a second input connected to said indicator electrode, and an output;
   a recorder connected to said output of said amplifier;
   a compressor having a nozzle for supplying the air to be tested to said sensor member of said indicator electrode, said compressor being coupled to the nozzle.

2. An apparatus according to claim 1, comprising said means for supplying the electrolyte which is in the form of an air lift immersed in said electrolyte of said second compartment, the air lift having an inlet; a switch connecting said compressor to said inlet of said air lift and to said nozzle for supplying the air being tested to said sensor member of said indicator electrode, said switch connecting said compressor to said air lift in one position and connecting said compressor to said nozzle in the other position.

3. An apparatus according to claim 2, comprising a control unit having a first output and a second output, and an electromagnetic valve which is said switch; said electromagnetic valve being connected to said first output of said control unit; a relay having a winding connected to said second output of said control unit and normally open contacts which are connected to said indicator electrode and to said comparison electrode.

4. An apparatus according to claim 1 wherein said sensor members of said indicator electrode and said comparison electrode are made of gold or silver sulfide.

* * * * *